(12) United States Patent
Imai

(10) Patent No.: US 10,918,360 B2
(45) Date of Patent: Feb. 16, 2021

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Yoshiro Imai, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 475 days.

(21) Appl. No.: 15/881,040

(22) Filed: Jan. 26, 2018

(65) Prior Publication Data
US 2018/0146956 A1 May 31, 2018

Related U.S. Application Data

(63) Continuation of application No. PCT/JP2016/063873, filed on May 10, 2016.

(30) Foreign Application Priority Data

Aug. 21, 2015 (JP) ................................. 2015-164045

(51) Int. Cl.
*A61B 8/00* (2006.01)
*A61B 8/08* (2006.01)
*A61B 8/14* (2006.01)

(52) U.S. Cl.
CPC .................. *A61B 8/54* (2013.01); *A61B 8/14* (2013.01); *A61B 8/4245* (2013.01); *A61B 8/52* (2013.01); *A61B 8/5207* (2013.01); *A61B 8/5223* (2013.01)

(58) Field of Classification Search
None
See application file for complete search history.

(56) References Cited

U.S. PATENT DOCUMENTS

| 2007/0112266 A1* | 5/2007 | Kishimoto | A61B 8/546 600/437 |
| 2009/0226062 A1* | 9/2009 | Nakamura | G06F 16/51 382/128 |

(Continued)

FOREIGN PATENT DOCUMENTS

| JP | 4-224738 A | 8/1992 |
| JP | 2010-259662 A | 11/2010 |

(Continued)

OTHER PUBLICATIONS

International Preliminary Report on Patentability and Written Opinion of the International Searching Authority (Forms PCT/IB/373 and PCT/ISA/237) for Application No. PCT/JP2016/063873, dated Feb. 27, 2018, with an English translation.

(Continued)

*Primary Examiner* — Joel F Brutus
(74) *Attorney, Agent, or Firm* — Birch, Stewart, Kolasch & Birch, LLP

(57) ABSTRACT

An ultrasound diagnostic apparatus includes: an ultrasound probe; an imaging unit that transmits and receives an ultrasound beam to and from a subject using the ultrasound probe and converts a received signal output from the ultrasound probe into an image to generate an ultrasound image of the subject, according to set imaging conditions; a part determination unit that determines an imaging part of the subject using the ultrasound image generated by the imaging unit; a determination result storage unit that stores determination results corresponding to a plurality of frames obtained by the part determination unit; and a determination result integration unit that integrates the determination results corresponding to the plurality of frames stored in the determination result storage unit and outputs an integrated determination result.

14 Claims, 6 Drawing Sheets

(56) References Cited

U.S. PATENT DOCUMENTS

2009/0318809 A1* 12/2009 Okamura ................ A61B 8/14
                                                    600/443
2015/0065916 A1*  3/2015 Maguire ................ A61B 34/32
                                                    600/573
2015/0178921 A1   6/2015 Hashimoto et al.

FOREIGN PATENT DOCUMENTS

JP        2012-205610 A     10/2012
JP         2014-61291 A      4/2014

OTHER PUBLICATIONS

International Search Report and English translation (Form PCT/ISA/210) for Application No. PCT/JP2016/063873, dated Jun. 21, 2016.
Extended European Search Report dated Jul. 20, 2018 for Application No. 16838850.2.

* cited by examiner

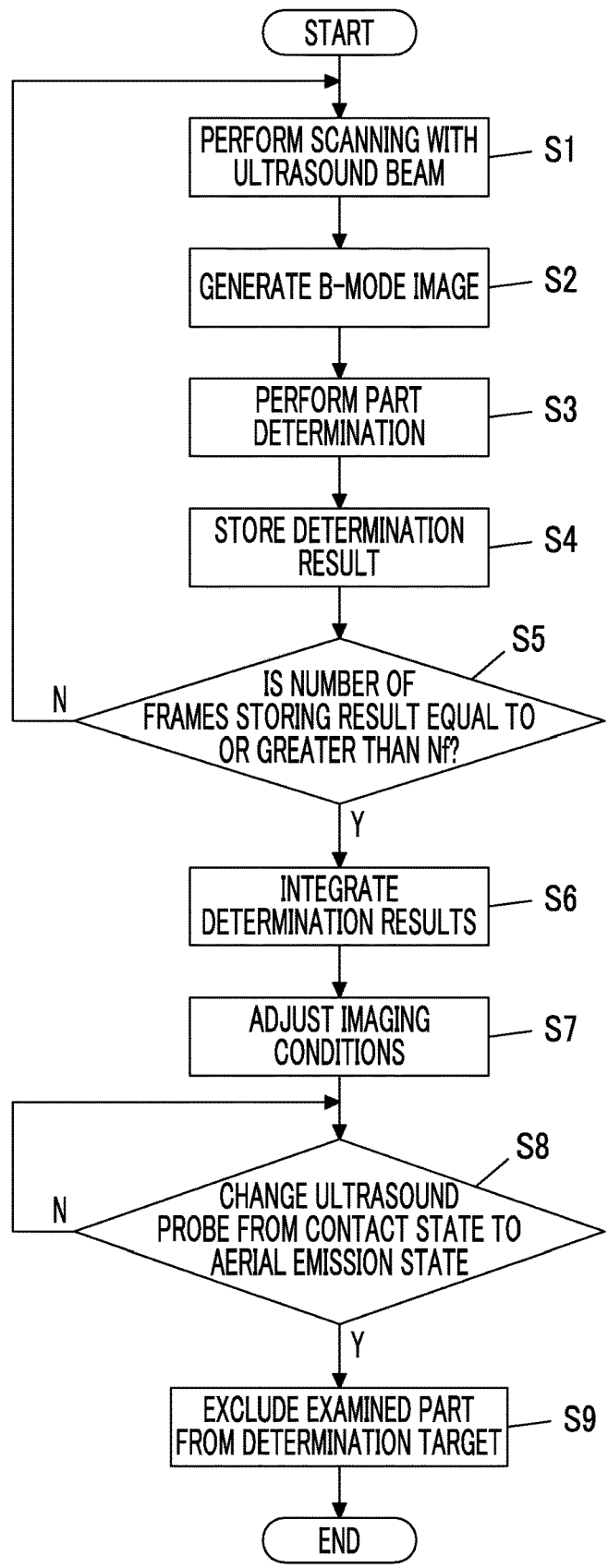

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2016/063873 filed on May 10, 2016, which claims priority under 35 U.S.C. § 119(a) to Japanese Patent Application No. 2015-164045 filed on Aug. 21, 2015. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that determines an imaging part of a subject on the basis of an ultrasound image.

2. Description of the Related Art

In the related art, an ultrasound diagnostic apparatus using an ultrasound image has been put to practical use in the medical field. In general, in this type of ultrasound diagnostic apparatus, an ultrasound probe provided with an array transducer scans a subject with an ultrasound beam and receives ultrasound echoes from the subject and the received signal is electrically processed to generate an ultrasound image.

In a case in which the ultrasound diagnostic apparatus is used to diagnose a plurality of imaging parts of the subject, appropriate imaging conditions vary depending on imaging parts in order to obtain ultrasound images suitable for diagnosis for each imaging part. Therefore, for example, JP1992-224738A (JP-H04-224738A) discloses an ultrasound diagnostic apparatus which automatically determines an imaging part from a generated ultrasound image, using a pattern matching process, and sets a scanning parameter most suitable for the imaging part on the basis of the determination result.

SUMMARY OF THE INVENTION

However, the shape of the same imaging part changes depending on the person. In addition, for example, brightness or a dynamic range varies depending on the difference between transmission characteristics and reflection characteristics for ultrasound beams. Therefore, in a case in which an imaging part is automatically determined by the apparatus disclosed in JP1992-224738A (JP-H04-224738A), there is a concern that an error in the determination result will occur. In a case in which erroneous determination is performed, a scanning parameter that is not suitable for the imaging part is set, which makes it difficult to obtain a good ultrasound image.

In a case in which erroneous part determination is performed during scanning with the ultrasound beam, the scanning parameter is instantaneously changed and the quality of an ultrasound image is changed. As a result, there is a concern that diagnosis will be hindered.

The invention has been made in order to solve the problems of the related art and an object of the invention is to provide an ultrasound diagnostic apparatus and a method for controlling the ultrasound diagnostic apparatus that can improve the reliability of part determination.

An ultrasound diagnostic apparatus according to the invention comprises: an ultrasound probe; an imaging unit that transmits and receives an ultrasound beam to and from a subject using the ultrasound probe and converts a received signal output from the ultrasound probe into an image to generate an ultrasound image of the subject, according to set imaging conditions; a part determination unit that determines an imaging part of the subject using the ultrasound image generated by the imaging unit; a determination result storage unit that stores determination results corresponding to a plurality of frames obtained by the part determination unit; and a determination result integration unit that integrates the determination results corresponding to the plurality of frames stored in the determination result storage unit and outputs an integrated determination result.

Preferably, the ultrasound diagnostic apparatus further comprises: an imaging condition memory that stores a plurality of imaging conditions set for each of a plurality of imaging parts in advance; and an apparatus control unit that selects an imaging condition corresponding to the integrated determination result from the plurality of imaging conditions stored in the imaging condition memory and controls the imaging unit such that the ultrasound image is generated under the selected imaging condition.

The imaging unit may include a transmitting/receiving unit that transmits and receives the ultrasound beam according to ultrasound beam scanning conditions and an image generation unit that generates the ultrasound image from the received signal according to ultrasound image generation conditions. The imaging conditions may include the ultrasound beam scanning conditions and the ultrasound image generation conditions.

The determination result integration unit may integrate the determination results corresponding to the plurality of frames stored in the determination result storage unit under a majority rule to obtain the integrated determination result. In this case, the determination result integration unit may give a weight to a determination result corresponding to the latest frame among the determination results corresponding to the plurality of frames stored in the determination result storage unit and integrate the determination results under the majority rule.

The part determination unit may output the determination result and a similarity score for each of the plurality of frames. The determination result integration unit may give weights to the determination results corresponding to the plurality of frames stored in the determination result storage unit according to the similarity scores output from the part determination unit and integrate the determination results under the majority rule.

The ultrasound diagnostic apparatus may further comprise an examined part storage unit that stores the integrated determination result. In a case in which a plurality of imaging parts of the subject are sequentially examined, the apparatus control unit may exclude the imaging part indicated by the integrated determination result stored in the examined part storage unit from the subsequent imaging parts to be determined by the part determination unit.

In this case, the ultrasound diagnostic apparatus may further comprise a probe state determination unit that determines whether the ultrasound probe is in an aerial emission state or a contact state with the subject. In a case in which the probe state determination unit determines that the ultrasound probe has been changed from the contact state with the subject to the aerial emission state, the apparatus control unit may store the integrated determination result in the examined part storage unit.

According to the invention, there is provided a method for controlling an ultrasound diagnostic apparatus including an ultrasound probe. The method comprises: a step of transmitting and receiving an ultrasound beam to and from a subject using the ultrasound probe and converting a received signal output from the ultrasound probe into an image to generate an ultrasound image of the subject, according to set imaging conditions; a step of determining an imaging part of the subject using the generated ultrasound image; a step of storing a plurality of frames of determination results for the imaging part; and a step of integrating the stored determination results corresponding to the plurality of frames and outputting an integrated determination result.

According to the invention, the determination results corresponding to a plurality of frames for an imaging part of the subject are stored. The stored determination results corresponding to the plurality of frames are integrated and the integrated determination result is output. Therefore, it is possible to improve the reliability of part determination.

BRIEF DESCRIPTION OF THE DRAWINGS

FIG. 9 is a flowchart illustrating the operation of Embodiment 2.

DESCRIPTION OF THE PREFERRED EMBODIMENTS

Hereinafter, embodiments of the invention will be described with reference to the accompanying drawings.

Embodiment 1

Figure 1:
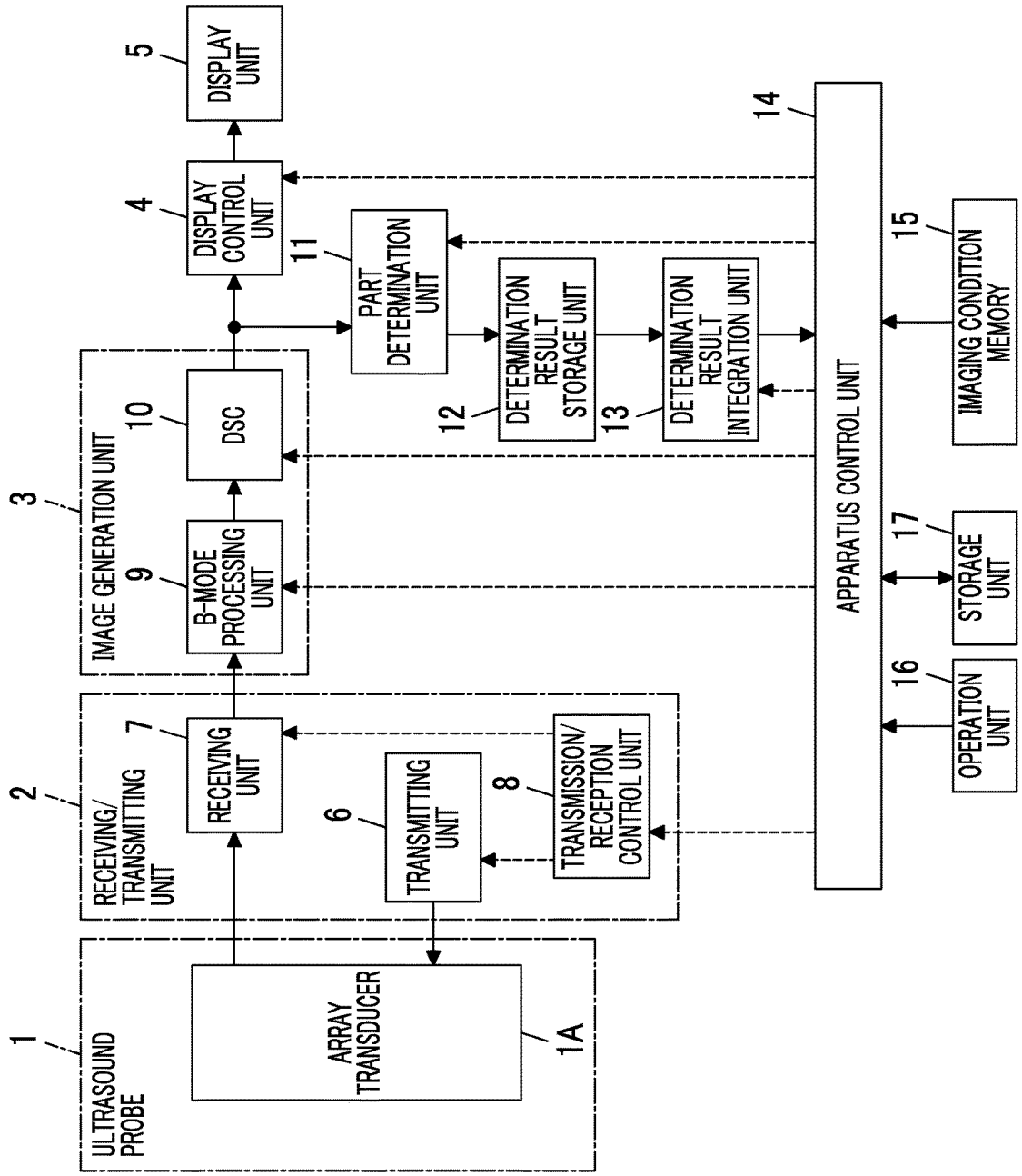
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. The ultrasound diagnostic apparatus includes an ultrasound probe 1 provided with an array transducer 1A. An image generation unit 3 is connected to the ultrasound probe 1 through a transmitting/receiving unit 2 and a display unit 5 is connected to the image generation unit 3 through a display control unit 4.

The transmitting/receiving unit 2 includes a transmitting unit 6 and a receiving unit 7 that are connected to the array transducer 1A of the ultrasound probe 1 and a transmission/reception control unit 8 that is connected to the transmitting unit 6 and the receiving unit 7. The image generation unit 3 includes a B-mode processing unit 9 that is connected to the receiving unit 7 of the transmitting/receiving unit 2 and a digital scan converter (DSC) 10 that is connected to the B-mode processing unit 9. The display control unit 4 is connected to the DSC 10.

A part determination unit 11 is connected to the DSC 10 of the image generation unit 3. A determination result storage unit 12 is connected to the part determination unit 11. In addition, a determination result integration unit 13 is connected to the determination result storage unit 12.

An apparatus control unit 14 is connected to the transmission/reception control unit 8 of the transmitting/receiving unit 2, the B-mode processing unit 9 and the DSC 10 of the image generation unit 3, the display control unit 4, the part determination unit 11, and the determination result integration unit 13. An imaging condition memory 15, an operation unit 16, and a storage unit 17 are connected to the apparatus control unit 14.

The array transducer 1A of the ultrasound probe 1 includes a plurality of ultrasound transducers that are one-dimensionally or two-dimensionally arranged. Each of the ultrasound transducers transmits ultrasonic waves in response to a driving signal supplied from the transmitting unit 6. In addition, each of the ultrasound transducers receives ultrasound echoes from a subject and outputs a received signal. Each ultrasound transducer is, for example, a transducer in which electrodes are formed on both sides of a piezoelectric body made of piezoelectric ceramic typified by lead zirconate titanate (PZT), a polymer piezoelectric element typified by polyvinylidene difluoride (PVDF), or piezoelectric single crystal typified by lead magnesium niobate-lead titanate (PMN-PT).

In a case in which a pulsed voltage or a continuous-wave voltage is applied to the electrodes of the transducer, the piezoelectric body is expanded and contracted, and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal.

The transmitting/receiving unit 2 transmits and receives an ultrasound beam according to the set ultrasound beam scanning conditions and the image generation unit 3 generates a B-mode image signal according to the set ultrasound image generation conditions. Therefore, the transmitting/receiving unit 2 and the image generation unit 3 form an imaging unit. In addition, imaging conditions for the imaging unit include the ultrasound beam scanning conditions for the transmitting/receiving unit 2 and the ultrasound image generation conditions for the image generation unit 3.

The transmitting unit 6 of the transmitting/receiving unit 2 includes, for example, a plurality of pulse generators, adjusts the amount of delay of each driving signal such that the ultrasonic waves transmitted from a plurality of ultrasound transducers in the array transducer 1A form an ultrasound beam on the basis of a transmission delay pattern selected according to a control signal from the transmission/reception control unit 8, and supplies the driving signals to the plurality of ultrasound transducers.

Figure 2:
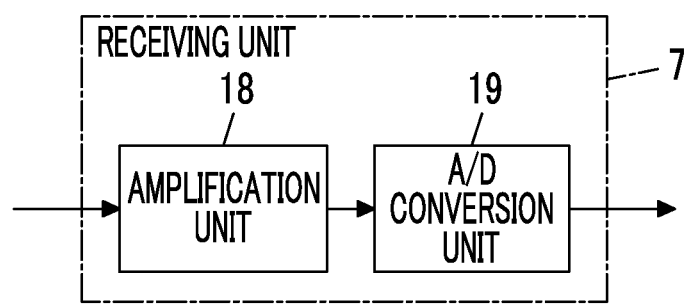
FIG. 2 is a block diagram illustrating the internal configuration of a receiving unit.

As illustrated in FIG. 2, the receiving unit 7 has a configuration in which an amplification unit 18 and an analog/digital (A/D) conversion unit 19 are sequentially connected in series. The receiving unit 7 amplifies the received signals transmitted from each ultrasound transducer of the array transducer 1A with the amplification unit 18 and performs A/D conversion for the received signals with the A/D conversion unit 19 to generate digital received data.

The transmission/reception control unit 8 controls the transmitting unit 6 and the receiving unit 7 on the basis of various control signals transmitted from the apparatus control unit 14 such that the transmission of an ultrasound pulse to a subject and the reception of an ultrasound echo from the subject are repeated at a pulse repetition frequency (PRF) interval.

Figure 3:
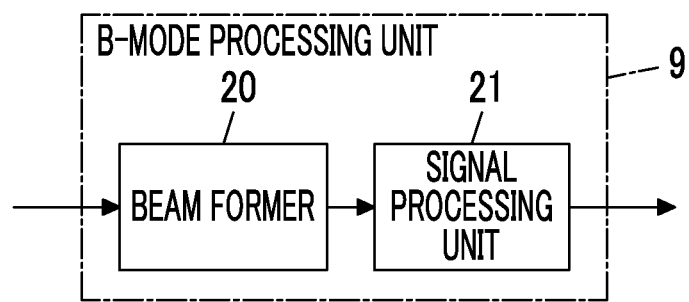
FIG. 3 is a block diagram illustrating the internal configuration of a B-mode processing unit.

The B-mode processing unit 9 of the image generation unit 3 has a configuration in which a beam former 20 and a signal processing unit 21 are sequentially connected in series, as illustrated in FIG. 3. The beam former 20 applies a delay to each received data item output from the receiving unit 7 of the transmitting/receiving unit 2 according to a sound speed or a sound speed distribution set on the basis of a reception delay pattern selected according to a control signal from the apparatus control unit 14 and adds the received data to perform a reception focusing process. A sound ray signal in which the focus of an ultrasound echo subjected to phasing addition is narrowed is generated by the reception focusing process.

The signal processing unit 21 corrects the attenuation of the sound ray signal generated by the beam former 20 depending on a distance according to the depth of the reflection position of ultrasonic waves and then performs an envelope detection process. In addition, the signal processing unit 21 performs various types of necessary image processing including a gradation process to generate a B-mode image signal which is tomographic image information about the issues of the subject.

The DSC 10 of the image generation unit 3 converts the B-mode image signal generated by the signal processing unit 21 into an image signal based on a general television signal scanning system (raster conversion).

The display control unit 4 displays a B-mode image on the display unit 5 on the basis of the B-mode image signal generated by the image generation unit 3.

The display unit 5 includes a display device, such as a liquid crystal display (LCD), and displays the B-mode image under the control of the display control unit 4.

The part determination unit 11 determines an imaging part of the subject on the basis of the B-mode image signal generated by the image generation unit 3.

The determination result storage unit 12 stores the determination results corresponding to a plurality of frames obtained by the part determination unit 11.

The determination result integration unit 13 integrates the determination results corresponding to the plurality of frames stored in the determination result storage unit 12 and outputs an integrated determination result.

The apparatus control unit 14 controls the transmission/reception control unit 8, the B-mode processing unit 9, the DSC 10, the display control unit 4, the part determination unit 11, and the determination result integration unit 13 on the basis of commands input by the operator through the operation unit 16.

The imaging condition memory 15 stores a plurality of imaging conditions which are set for a plurality of imaging parts of the subject in advance. The imaging conditions are used to acquire the B-mode images suitable for diagnosing each corresponding imaging part.

The operation unit 16 is used by the operator to perform an input operation and may include, for example, a keyboard, a mouse, a trackball, and a touch panel.

The storage unit 17 stores, for example, an operation program. For example, a recording medium, such as a hard disk, a flexible disk, an MO, an MT, a RAM, a CD-ROM, a DVD-ROM, an SD card, a CF card, or a USB memory, or a server may be used as the storage unit 17.

Here, a part determination method in the part determination unit 11 will be described.

Examples of the imaging part of the subject can include the heart, the right abdomen, the left abdomen, and the urinary bladder. Of course, the part determination unit 11 may be configured so as to determine various other imaging parts.

The part determination unit 11 stores the typical pattern data of a plurality of imaging parts in advance and calculates the similarity between the B-mode image signal of the imaging part output from the DSC 10 of the image generation unit 3 and each of a plurality of pattern data items stored in advance. A known matching technique can be used to calculate the similarity. In addition to the matching technique, for example, the following method may be used to calculate the similarity: a machine learning method disclosed in Csurka et al.: Visual Categorization with Bags of Keypoints, Proc. of ECCV Workshop on Statistical Learning in Computer Vision, pp. 59-74 (2004); or a general image recognition method using deep learning disclosed in Krizhevsk et al.: ImageNet Classification with Deep Convolutional Neural Networks, Advances in Neural Information Processing Systems 25, pp. 1106-1114 (2012).

The part determination unit 11 calculates similarity scores between the B-mode image signal of the imaging part and a plurality of imaging parts, using these methods, and uses an imaging part with the highest similarity score as the determination result. For example, in a case in which the similarity score for the heart is 5, the similarity score for the right abdomen is 10, the similarity score for the left abdomen is 6, and the similarity score for the urinary bladder is 3, the determination result indicating that the captured imaging part is the right abdomen with the highest similarity score is obtained.

In this case, the following configuration may be used: before the part is determined, the operator inputs subject information (for example, a body type and sex) through the operation unit 16 and pattern data used to determine the part is changed according to the subject information. That is, a plurality of pattern data items corresponding to, for example, a difference in body size and sex are stored for each imaging part and the part is determined on the basis of pattern data corresponding to the input subject information. With this configuration, it is possible to prevent an error in determination caused by the difference in the body size and sex of the subject and to improve the accuracy of determining the part.

The determination of the part by the part determination unit 11 may be performed for each display frame of the B-mode image or may be performed for every several frames for one imaging part.

As such, the determination results corresponding to a plurality of frames obtained by the part determination unit 11 are stored for one imaging part in the determination result storage unit 12.

The determination result integration unit 13 integrates the determination results corresponding to a plurality of frames stored in the determination result storage unit 12 and outputs an integrated determination result. However, a majority rule may be used as the method for integrating the determination results. For example, in a case in which Nf determination results corresponding to Nf frames are stored for one imaging part in the determination result storage unit 12, an imaging part indicated by the largest number of determination results among the Nf determination results, that is, an imaging part with the highest score is output as the integrated determination result. As such, since the determination results corresponding to a plurality of frames are integrated under the majority rule to obtain the integrated determination result, it is possible to effectively prevent an error in determination.

In addition, in this embodiment, the determination results corresponding to a plurality of frames stored in the determination result storage unit 12 are simply integrated under the majority rule. However, a weight may be given to the latest frame and the determination results may be integrated under the majority rule. That is, weights may be given to the determination results corresponding to a predetermined number of frames stored in the determination result storage unit 12 in reverse chronological order among the determination results corresponding to a plurality of frames stored in the determination result storage unit 12 and the determination results may be integrated under the majority rule. The weight given to the determination result corresponding to a new frame stored in the determination result storage unit 12 may be greater than the weight given to the determination result corresponding to an old frame among the determination results corresponding to a plurality of frames stored in the determination result storage unit 12.

For example, Nf is 90 and, among 90 determination results, a weight of 3 is given to the determination results corresponding to 30 new frames, a weight of 2 is given to the determination results corresponding to 30 intermediate frames, and a weight of 1 is given to the determination results corresponding to 30 old frames. Then, an imaging part with the highest score is output as the integrated determination result. In a case in which the imaging part is changed, the position of the ultrasound probe 1 is not determined immediately after the change and the quality of the B-mode image is unstable. For this reason, a weight is given to the latest frame. Therefore, it is possible to reduce a time lag in a case in which the imaging part is changed and to more rapidly perform accurate part determination.

In addition, weighting may be performed according to the similarity score during part determination and the determination results may be integrated under the majority rule. For example, in a case in which Nf is 90, the number of determination results indicating an imaging part A among 90 determination results is 45, the number of determination results indicating an imaging part B is 45, the average value of the similarity scores in 45 determination results indicating the imaging part A is 10, the average value of the similarity scores in 45 determination results indicating the imaging part B is 5, and the number of determination results is multiplied by the average value of the similarity scores to calculate a score, the score of the imaging part A is 10×45=450 and the score of the imaging part B is 5×45=225. Therefore, the imaging part A with a higher score is output as the integrated determination result. As such, since weighting is performed according to the similarity score, it is possible to further increase the accuracy of determining the part.

Figure 4:
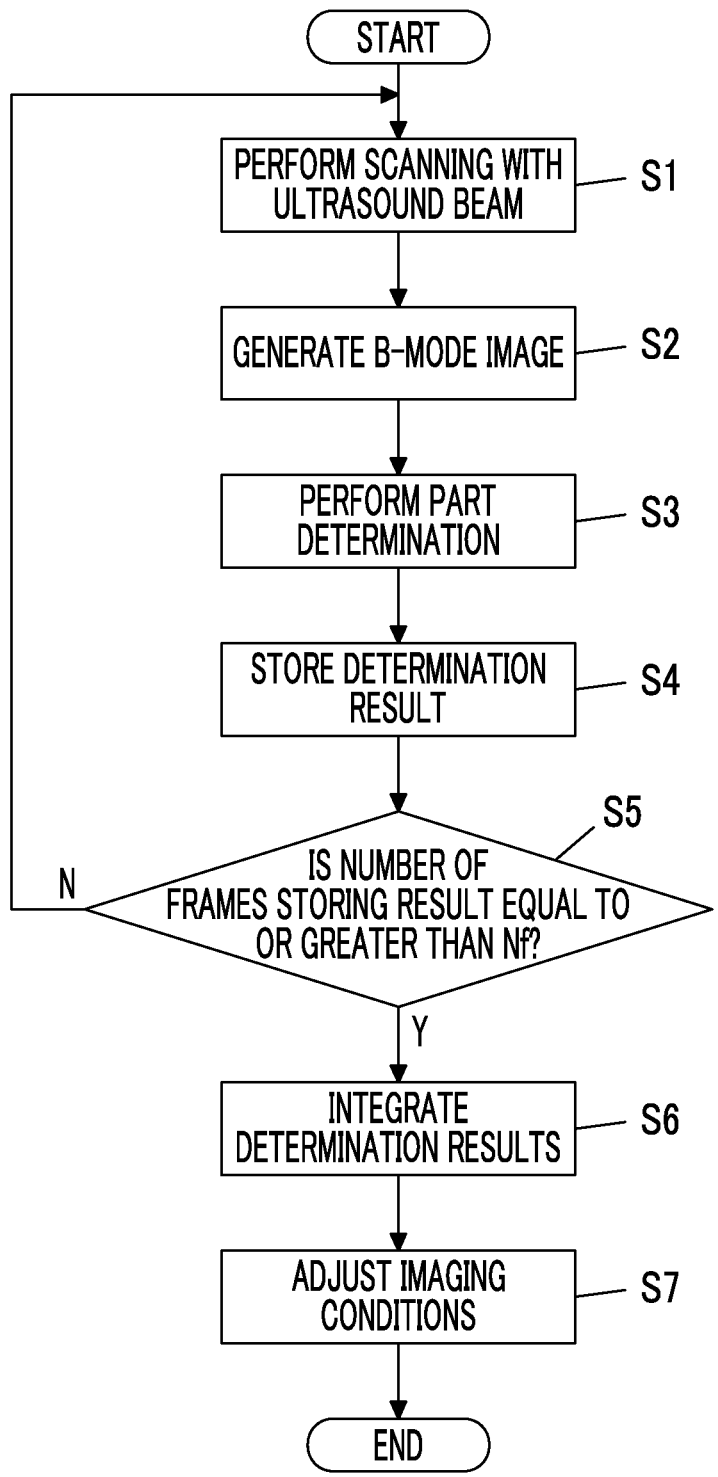
FIG. 4 is a flowchart illustrating the operation of Embodiment 1.

Next, the operation of Embodiment 1 will be described with reference to the flowchart illustrated in FIG. 4.

First, in Step S1, the transmitting/receiving unit 2 performs the transmission and reception of an ultrasound beam and scanning, using the plurality of ultrasound transducers in the array transducer 1A of the ultrasound probe 1. A received signal from each ultrasound transducer that has received ultrasound echoes from the subject is output to the receiving unit 7. The receiving unit 7 performs amplification and A/D conversion for the received signal to generate received data.

In Step S2, the received data is input to the image generation unit 3. The B-mode processing unit 9 performs the reception focusing process for the received data and the DSC 10 converts signal conversion to generate a B-mode image signal. The B-mode image signal is output from the image generation unit 3 to the display control unit 4. The B-mode image is displayed on the display unit 5.

The B-mode image signal output from the DSC 10 of the image generation unit 3 is input to the part determination unit 11. After the part is determined by the part determination unit 11 in Step S3, the determination results are stored in the determination result storage unit 12 in Step S4.

Then, in Step S5, it is determined whether the number of frames storing the determination results for one imaging part in the determination result storage unit 12 reaches a predetermined number of frames Nf. In a case in which the number of frames does not reach the number of frames Nf, the process returns to Step S1. In this way, Steps S1 to S5 are repeated until the number of frames storing the determination results reaches Nf.

Here, the number of frames Nf is predetermined. However, the operator may input the number of frames Nf through the operation unit 16.

In addition, instead of directly setting the number of frames Nf, the time for which the determination results are stored may be set to automatically determine the number of frames Nf according to a frame rate. For example, in a case in which the determination results corresponding to three seconds are stored and the frame rate is 30 frames/second, Nf is 30×3=90. In a case in which the frame rate is 40 frames/second, Nf is 40×3=120.

In a case in which it is determined in Step S5 that the number of frames storing the determination results reaches Nf, the process proceeds to Step S6 and the determination result integration unit 13 integrates the determination results corresponding to Nf frames stored in the determination result storage unit 12 and outputs an integrated determination result.

In a case in which the integrated determination result is output from the determination result integration unit 13 in this way, the apparatus control unit 14 adjusts imaging conditions in Step S7. That is, the apparatus control unit 14 selects imaging conditions corresponding to the integrated determination result from a plurality of imaging conditions which are stored in the imaging condition memory 15 in advance, on the basis of the integrated determination result output from the determination result integration unit 13, and controls the transmitting/receiving unit 2 and the image generation unit 3 such that imaging is performed for the subsequent frames under the selected imaging conditions. Specifically, the transmission/reception control unit 8 of the transmitting/receiving unit 2 is controlled such that an ultrasound beam is transmitted and received according to an ultrasound beam scanning condition included in the imaging conditions selected from the imaging condition memory 15 and the image generation unit 3 is controlled such that a B-mode image is generated from the received signal according to an ultrasound image generation condition included in the selected imaging conditions.

Among the imaging conditions, the ultrasound beam scanning condition can include an ultrasound beam transmission frequency, a focal position, and a display depth and the ultrasound image generation condition can include a sound speed, detection conditions, a gain, a dynamic range, a gradation curve, speckle reduction intensity, and the degree of edge enhancement. Appropriate conditions for each imaging part are in the imaging condition memory 15 in advance.

Embodiment 2

Figure 5:
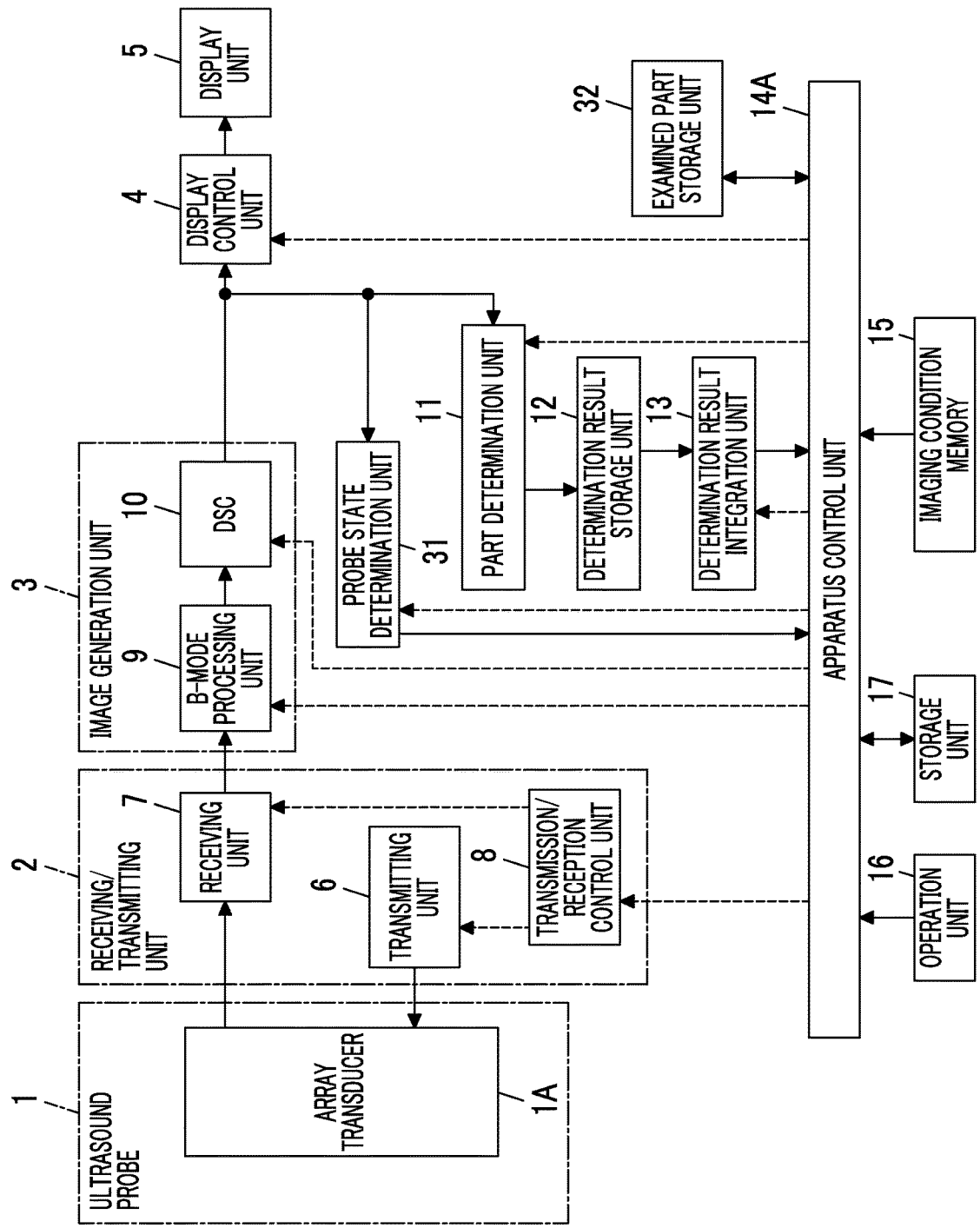
FIG. 5 is a block diagram illustrating the configuration of an ultrasound diagnostic apparatus according to Embodiment 2.

FIG. 5 illustrates the configuration of an ultrasound diagnostic apparatus according to Embodiment 2. The ultrasound diagnostic apparatus differs from the ultrasound diagnostic apparatus according to Embodiment 1 illustrated in FIG. 1 in that an apparatus control unit 14A is provided instead of the apparatus control unit 14, a probe state determination unit 31 is connected to the DSC 10 of the image generation unit 3 and the apparatus control unit 14A, and an examined part storage unit 32 is connected to the apparatus control unit 14A.

The probe state determination unit 31 determines whether the ultrasound probe 1 is in a contact state in which the ultrasound probe 1 comes into contact with the body surface of a subject and emits ultrasonic waves into the body of the subject or an aerial emission state in which the ultrasound probe 1 is separated from the body surface of the subject and emits ultrasonic waves to the air, on the basis of the B-mode image generated by the image generation unit 3.

The examined part storage unit 32 stores an examined imaging part among a plurality of imaging parts.

The apparatus control unit 14A has a function that stores an imaging part indicated by the integrated determination result output from the determination result integration unit 13 as the examined part in the examined part storage unit 32 in a case in which the probe state determination unit 31 determines that the state of the ultrasound probe 1 has been changed and excludes the imaging part from the next part determination targets, in addition to the functions of the apparatus control unit 14 according to Embodiment 1.

Figure 6:
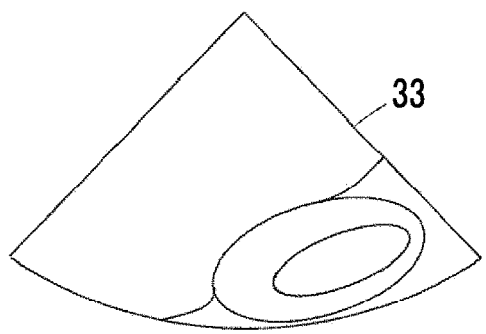
FIG. 6 is a diagram illustrating a B-mode image in Embodiment 2.

The probe state determination unit 31 may analyze the B-mode image generated by the image generation unit 3 to determine whether the ultrasound probe 1 is in the contact state with the subject or the aerial emission state. In general, in a case in which the ultrasound probe 1 comes into contact with the body surface of the subject and emits ultrasonic waves into the body of the subject, a certain structure, that is, a tissue of the subject is visualized in a B-mode image 33 as illustrated in FIG. 6. However, in a case in which the ultrasound probe 1 is separated from the body surface of the subject and emits ultrasonic waves to the air, no structure is visualized in the B-mode image 33.

Therefore, it is detected whether a structure is present or absent in the B-mode image 33 on the basis of a brightness distribution of the B-mode image 33. In a case in which a structure is detected in the B-mode image 33, it can be determined that the ultrasound probe 1 is in the contact state with the subject. In a case in which no structure is detected in the B-mode image 33, it can be determined that the ultrasound probe 1 is in the aerial emission state.

Figure 7:
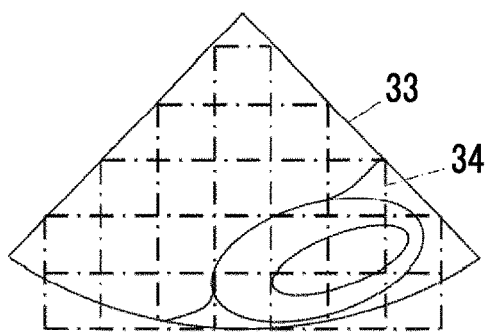
FIG. 7 is a diagram illustrating a B-mode image in which a plurality of regions of interest are set.

Specifically, as illustrated in FIG. 7, the B-mode image 33 is divided into a plurality of regions 34. The variance of the brightness of each region 34 or the difference between the maximum brightness and the minimum brightness is calculated as an index value. In a case in which the number of regions 34 with an index value that is equal to or greater than a predetermined set value is equal to or greater than a predetermined threshold value, the probe state determination unit 31 determines that the ultrasound probe 1 is in the contact state with the subject. On the other hand, in a case in which the number of regions 34 with an index value that is equal to or greater than the predetermined set value is less than the predetermined threshold value, the probe state determination unit 31 determines that the ultrasound probe 1 is in the aerial emission state.

Figure 8:
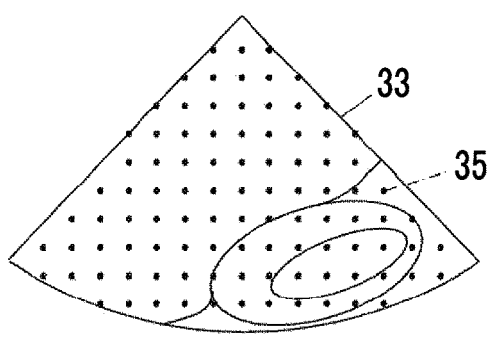
FIG. 8 a diagram illustrating a B-mode image in which a plurality of observation points are set.

In addition to the analysis based on the index value of the brightness of each region 34, a plurality of observation points 35 may be set in the B-mode image 33 as illustrated in FIG. 8 and the amount of movement of each observation point 35 between frames may be detected to determine the state of the ultrasound probe 1.

In a case in which the number of observation points 35 of which the amount of movement between frames is equal to or less than a set value is equal to or greater than a predetermined threshold value, the probe state determination unit 31 may determine that the movement of the ultrasound probe 1 is stable and may determine whether the ultrasound probe 1 is in the contact state with the subject or the aerial emission state on the basis of the index value of the brightness of each region 34.

In a case in which the ultrasound probe 1 is in the aerial emission state, it is considered that almost the same B-mode image is acquired. Therefore, the B-mode image in a case in which the ultrasound probe 1 is in the aerial emission state may be stored in advance and the probe state determination unit 31 may determine the state of the ultrasound probe 1, using a matching technique such as template matching.

Next, the operation of Embodiment 2 will be described with reference to the flowchart illustrated in FIG. 9. As in Embodiment 1, in Steps S1 to S7, the determination of the part by the part determination unit 11, the integration of the determination results by the determination result integration unit 13, and the adjustment of the imaging conditions by the apparatus control unit 14A are performed. Then, in Step S8, the probe state determination unit 31 determines whether the ultrasound probe 1 has been changed from the contact state with the subject to the aerial emission state.

Then, in a case in which it is determined that the ultrasound probe 1 has been changed from the contact state with the subject to the aerial emission state, the process proceeds to Step S9 and the apparatus control unit 14A detects that the image part to be examined has been changed to the next imaging part, recognizes the imaging part indicated by the integrated determination result output from the determination result integration unit 13 in Step S6 as an examined part, stores the imaging part in the examined part storage unit 32, and excludes the stored integrated determination result (That is, the examined part) from the subsequent part determination targets.

Similarity determination may not be performed for the examined part stored in the examined part storage unit 32 in the subsequent part determination process. Alternatively, similarity determination may be performed for the examined part. In a case in which the determination result integration unit 13 reads out the determination results from the determination result storage unit 12 and integrates the determination results, a weight given to the examined part may be reduced and the determination results may be integrated under the majority rule.

In addition, the operator may designate an imaging part to be excluded from the part determination targets through the operation unit 16.

As such, the ultrasound diagnostic apparatus according to Embodiment 2 recognizes the examined part and excludes the examined part from the subsequent part determination targets. Therefore, in a case in which a plurality of imaging parts are sequentially examined in a predetermined order as in a focused assessment with sonography for trauma (FAST) examination in critical care, it is possible to rapidly perform part determination for the subsequent imaging parts with high accuracy.

EXPLANATION OF REFERENCES

1: ultrasound probe
1A: array transducer
2: transmitting/receiving unit
3: image generation unit
4: display control unit
5: display unit
6: transmitting unit
7: receiving unit
8: transmission/reception control unit
9: B-mode processing unit
10: DSC
11: part determination unit
12: determination result storage unit
13: determination result integration unit
14, 14A: apparatus control unit
15: imaging condition memory
16: operation unit
17: storage unit
18: amplification unit
19: A/D conversion unit
20: beam former
21: signal processing unit
31: probe state determination unit
32: examined part storage unit
33: B-mode image
34: region
35: observation point

What is claimed is:

1. An ultrasound diagnostic apparatus comprising:
an ultrasound probe; and
a processor configured to:
transmit and receive an ultrasound beam to and from a subject using the ultrasound probe and convert a received signal output from the ultrasound probe into an image to generate an ultrasound image of the subject, according to set imaging conditions;
determine an imaging part of the subject using the ultrasound image, thereby obtaining a determination result indicative of the imaging part that has been captured in a frame;
store a plurality of the determination results corresponding to a plurality of the frames in a determination result memory; and
integrate the determination results corresponding to the plurality of frames stored in the determination result memory and output the imaging part indicated by the largest number of the determination results among the plurality of the determination results as an integrated determination result.

2. The ultrasound diagnostic apparatus according to claim 1, further comprising:
an imaging condition memory that stores a plurality of imaging conditions set for each of a plurality of imaging parts in advance,
wherein the processor is further configured to select an imaging condition corresponding to the integrated determination result from the plurality of imaging conditions stored in the imaging condition memory and control such that the ultrasound image is generated under the selected imaging condition.

3. The ultrasound diagnostic apparatus according to claim 2,
wherein the processor is further configured to transmit and receive the ultrasound beam according to ultrasound beam scanning conditions and generate the ultrasound image from the received signal according to ultrasound image generation conditions, wherein
the imaging conditions include the ultrasound beam scanning conditions and the ultrasound image generation conditions.

4. The ultrasound diagnostic apparatus according to claim 2, further comprising:
an examined part memory that stores the integrated determination result,
wherein, when the plurality of imaging parts of the subject are sequentially examined, the processor is further configured to exclude the imaging part indicated by the integrated determination result stored in the examined part memory from the subsequent imaging parts to be determined.

5. The ultrasound diagnostic apparatus according to claim 4,
wherein the processor is further configured to determine whether the ultrasound probe is in an aerial emission state or a contact state with the subject, and
when it is determined that the ultrasound probe has been changed from the contact state with the subject to the aerial emission state, store the integrated determination result in the examined part storage unit.

6. The ultrasound diagnostic apparatus according to claim 1,
wherein the processor is further configured to transmit and receive the ultrasound beam according to ultrasound beam scanning conditions and generate the ultrasound image from the received signal according to ultrasound image generation conditions, wherein
the imaging conditions include the ultrasound beam scanning conditions and the ultrasound image generation conditions.

7. The ultrasound diagnostic apparatus according to claim 1,
wherein the processor is further configured to give a weight to the determination result corresponding to the latest frame among the determination results corresponding to the plurality of frames stored in the determination result memory and integrate the determination results.

8. The ultrasound diagnostic apparatus according to claim 1,
wherein the processor is further configured to output the determination result and similarity scores for the plurality of frames, and
give weights to the determination results corresponding to the plurality of frames stored in the determination result memory according to the similarity scores and integrate the determination results.

9. A method for controlling an ultrasound diagnostic apparatus including an ultrasound probe, the method comprising:
a step of transmitting and receiving an ultrasound beam to and from a subject using the ultrasound probe and converting a received signal output from the ultrasound probe into an image to generate an ultrasound image of the subject, according to set imaging conditions;
a step of determining an imaging part of the subject using the generated ultrasound image, thereby obtaining a determination result indicative of the imaging part that has been captured in a frame;

a step of storing a plurality of determination results corresponding to a plurality of frames for the imaging part; and a step of integrating the stored determination results corresponding to the plurality of frames and outputting the imaging part indicated by the largest number of determination results among the plurality of determination results as an integrated determination result.

10. The method for controlling an ultrasound diagnostic apparatus according to claim 9, wherein a plurality of imaging conditions set for each of a plurality of imaging parts are stored in advance, and an imaging condition corresponding to the integrated determination result are selected from the plurality of imaging conditions stored and the ultrasound image is generated under the selected imaging condition.

11. The method for controlling an ultrasound diagnostic apparatus according to claim 10, wherein the integrated determination result is stored, and when the plurality of imaging parts of the subject are sequentially examined, the imaging part indicated by the integrated determination result stored is excluded from the subsequent imaging parts to be determined.

12. The method for controlling an ultrasound diagnostic apparatus according to claim 9, wherein the imaging conditions include ultrasound beam scanning conditions used to transmit and receive the ultrasound beam and ultrasound image generation conditions used to generate the ultrasound image from the received signal.

13. The method for controlling an ultrasound diagnostic apparatus according to claim 9, wherein a weight is given to a determination result corresponding to the latest frame among the determination results corresponding to the plurality of frames stored and the determination results are integrated.

14. The method for controlling an ultrasound diagnostic apparatus according to claim 9, wherein the determination result and a similarity score are output for each of the plurality of frames, and weights are given to the determination results corresponding to the plurality of frames stored according to the similarity scores output and the determination results are integrated.

* * * * *